(12) United States Patent
Taylor (10) Patent No.: US 10,939,671 B2
(45) Date of Patent: Mar. 9, 2021

(54) SELF-HARVESTING SUSTAINING FEED SYSTEM FOR AQUAPONICS

(71) Applicant: Gary De Andre Taylor, Kansas City, MO (US)

(72) Inventor: Gary De Andre Taylor, Kansas City, MO (US)

(73) Assignee: M2M COMMUNITY FOUNDATION, Kansas City, MO (US)

( * ) Notice: Subject to any disclaimer, the term of this patent is extended or adjusted under 35 U.S.C. 154(b) by 310 days.

(21) Appl. No.: 15/847,596

(22) Filed: Dec. 19, 2017

(65) Prior Publication Data

US 2018/0168133 A1  Jun. 21, 2018

Related U.S. Application Data

(60) Provisional application No. 62/436,348, filed on Dec. 19, 2016.

(51) Int. Cl.

| | | |
|---|---|---|
| *A01G 31/02* | (2006.01) | |
| *A01G 31/06* | (2006.01) | |
| *A01K 61/80* | (2017.01) | |
| *A01K 61/85* | (2017.01) | |
| *A01K 63/00* | (2017.01) | |
| *A01K 67/033* | (2006.01) | |
| *A01K 63/06* | (2006.01) | |
| *A01K 63/04* | (2006.01) | |

(52) U.S. Cl.
CPC ............ *A01K 61/85* (2017.01); *A01K 61/80* (2017.01); *A01K 63/003* (2013.01); *A01K 63/04* (2013.01); *A01K 63/065* (2013.01); *A01K 67/033* (2013.01); *A01G 31/02* (2013.01); *A01G 31/06* (2013.01); *Y02A 40/81* (2018.01); *Y02P 60/21* (2015.11); *Y02P 60/60* (2015.11)

(58) Field of Classification Search
CPC ........ A01G 31/00; A01G 31/02; A01G 31/06; A01K 61/80; A01K 61/85; A01K 63/00; A01K 63/003
USPC .......... 47/48.5, 59 R, 60, 62 R, 63; 119/226, 119/230, 246, 247
See application file for complete search history.

(56) References Cited

U.S. PATENT DOCUMENTS

| | | | | |
|---|---|---|---|---|
| 5,097,795 A * | 3/1992 | Adey | ..................... | A01K 63/04 119/226 |
| 5,775,260 A * | 7/1998 | Jansen | .................. | A01K 63/006 119/246 |
| 8,001,932 B2 * | 8/2011 | Kania | ..................... | A01K 61/70 119/217 |
| 8,966,816 B2 * | 3/2015 | Toone | ..................... | A01G 31/02 119/246 |
| 2003/0150394 A1 * | 8/2003 | Wolfe | .................. | A01K 63/003 119/246 |
| 2011/0296756 A1 * | 12/2011 | Zhang | ...................... | A01K 5/00 47/59 R |

(Continued)

*Primary Examiner* — David J Parsley
(74) *Attorney, Agent, or Firm* — Polsinelli PC (57) ABSTRACT

A self-harvesting sustaining feed system includes a tank for housing fish, a frame located above the fish tank, one or more plant floats which float atop water within shelves held by the frame, and an insect tray for housing larvae. Temporary temperature changes in the insect tray cause the larvae within the insect tray to migrate out and fall into the fish tank below.

14 Claims, 5 Drawing Sheets

(56) References Cited

U.S. PATENT DOCUMENTS

| | | | | |
|---|---|---|---|---|
| 2014/0047767 A1* | 2/2014 | Bodlovich | ................ | C02F 3/32 47/62 N |
| 2015/0250134 A1* | 9/2015 | Hicks | ....................... | A01K 1/03 119/246 |
| 2017/0042131 A1* | 2/2017 | Unger | .................. | A01K 67/033 |

* cited by examiner

SELF-HARVESTING SUSTAINING FEED SYSTEM FOR AQUAPONICS

CROSS REFERENCE TO RELATED APPLICATION

This application is related to and claims priority under 35 U.S.C. § 119(e) from U.S. Patent Application No. 62/436,348, entitled "SELF-HARVESTING SUSTAINING FEED SYSTEM FOR AQUAPONICS," which was filed Dec. 19, 2016 and is incorporated herein by reference in its entirety.

FIELD

The present disclosure relates to a system, apparatus, and method directed to a self-sustaining fish food source.

BACKGROUND

Aquaponics systems commonly grow both fish and plants in the same system. Fish grown using aquaponics techniques require fish food to grow. Fish may be fed living organisms such as insects, or insect larvae.

Fish in aquaponics systems are generally fed fish food manually. In some aquaponics systems, the fish are fed living insect larvae. In systems where fish are fed larvae, the larvae are manually fed to the fish by depositing an amount of larvae into a fish tank. While manually feeding larvae to fish, the larvae may escape causing waste. Further, manually feeding larvae to fish is time consuming making the process difficult to scale up.

What is needed is a system for automatically feeding larvae to fish without needing to manually harvest larvae.

It is with these issues in mind, among others, that various aspects of the disclosure were conceived.

SUMMARY

The purpose of this disclosure is to provide a self-harvesting sustaining feed system for an aquaponics system. The system includes a fish tank to house tilapia or other suitable fish. The system also includes a frame having center frame supports and side frame supports. The system further includes one or more plant floats. The plant floats have a plurality of apertures which allow a plant to be planted within each aperture. The apertures in the plant floats also provide an area that allows the roots of the plant to be in contact with the water beneath the plant float. The system also includes an insect tray. The insect tray may have slanted walls, which provide a surface that allows insect larva to migrate out of the tray when the temperature of the insect tray is altered. The system may also include one or more shelves which hold water in a manner that allows the insect tray or plant float to rest atop the water within the shelf. The system may also include a water heating system having at least one outlet pipe connected to the water heating system. The pipes of the water heating system may run through the water in the shelves, the insect tray, and the fish tank in order to control the temperature of the various components. The system may be used to control the temperature of the insect tray to cause larvae within the insect tray to migrate out of the insect tray by adjusting the temperature of the water beneath the insect tray by increasing or decreasing the temperature of the heat pump unit.

In an embodiment, a self-harvesting sustaining feed system includes a tank for housing fish, a frame located above the fish tank, one or more plant floats which float atop water within shelves held by the frame, and an insect tray for housing larvae. Temporary temperature changes in the insect tray cause the larvae within the insect tray to migrate out and fall into the fish tank below.

In another embodiment, a self-harvesting sustaining feed system for an aquaponics system includes a tank, a frame above the tank, one or more plant floats in communication with the frame, an insect tray held by the frame, the insect tray having slanted walls, and one or more shelves held by the frame.

In another embodiment, a method for providing self-harvesting sustaining feed for aquaponics uses a tank and an insect tray containing larvae. The insect tray is in communication with water. The method includes monitoring a temperature of water in the tank, determining whether fish within the tank need food, adjusting the temperature of water, and causing larvae within the insect tray to migrate out of the insect tray.

These and other aspects, features, and benefits of the present disclosure will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate embodiments and/or aspects of the disclosure and, together with the written description, serve to explain the principles of the disclosure. Wherever possible, the same reference numbers are used throughout the drawings to refer to the same or like elements of an embodiment, and wherein.

DETAILED DESCRIPTION

For the purpose of promoting an understanding of the principles of the present disclosure, reference will now be made to the embodiments illustrated in the drawings, and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates.

It is to be understood that the disclosed embodiments are merely exemplary of the self-sustaining fish food system, which may be embodied in various forms. Therefore, specific structural and functional details disclosed herein are not to be interpreted as limiting, but merely as a basis for the claims and as a representative basis for teaching one skilled in the art to variously employ the present system in virtually any appropriately detailed structure.

FIG. 1 through FIG. 5 illustrate various embodiments of an aquaponics unit 1 of the present disclosure. The aquaponics unit 1 comprises a generally rectangular prism frame 50 that supports the aquaponics unit 1. One or more shelves 200A-C are attached to the frame. A plant float 600A-C may float on the water within each shelf 200 A-C. The aquaponics unit 1 may also include a tank 300 located below the frame. In one embodiment, the tank 300 may be a fish tank or another type of tank. The tank may be constructed of glass or another type of material. The aquaponics unit 1 may have an insect tray 500 that floats atop the water within the shelf 200 C. The insect tray may also be attached to the frame at frame corner supports 52A-D and frame center supports 54A-B. The aquaponics unit 1 additionally includes a heat pump 400 for pumping temperature controlled water through the aquaponics unit 1.

The frame 50 may have a rectangular configuration or another suitable configuration. Because the frame 50 provides support for the aquaponics unit 1, the frame 50 may be made of a material that is rigid enough to provide support. The frame 50 may be made of a rigid or semi-rigid material such as a metal or a plastic, or a combination of metals and plastics. The frame 50 preferably has a rectangular shape, but may be other shapes such as a square shape. The frame 50 may have at least four corner supports 52 A-D and center supports 54 A-B. Both the corner supports 52 A-D and the center supports 54 A-B are vertical poles that make up the frame. The corner supports 52 A-D and the center supports 54 A-B may be configured for engaging and for attaching shelves 200 A-C. The frame 50 may have dimensions that are appropriate for accommodating various sizes of shelves. As a non-limiting example, the frame 50 may have a height of 10 feet, a width of 6 feet, and a depth of 4 feet. The frame 50 may also have a height of 12 feet, a width of 8 feet, and a depth of 6 feet.

The aquaponics unit 1 may include shelves 200 A-C. The shelves 200 A-C are attached to the frame 50 at frame corner supports 52A-D and frame center supports 54A-B. The shelves 200A-C of the aquaponics unit 1 are configured to hold water. In this regard, the shelves may be made of a material that is impervious or nearly impervious to water or other liquids. The shelves 200 A-C may be lined with plastic, rubber, or other waterproof materials. One or more of the shelves 200 A-C may include a bed of gravel 640 that acts as a natural filtration system to fish waste that is pumped through the one or more shelves 200 A-C. One of skill in the art will appreciate that the bed of gravel 640 may be any natural filtration system known in the art. The shelves 200 A-C may have a top surface and a bottom surface. The bottom surface of the shelf 200 A-C may be configured to house a lighting source or another suitable light source. The lighting source may be florescent lights. One of skill in the art will appreciate that the lighting source may be incandescent lights, halogen lights, light emitting diode (LED) lights, or any other lighting source for providing light for growing plants 700. The shelves 200A-C may be tilted in order to allow water to flow out of the shelves 200 A-C. The shelves 200 A-C should have dimensions that are appropriate for holding water and for being received by the frame 50. As a non-limiting example, the shelves 200 A-C may have a height of 1 foot, a width of 5 feet 10 inches, and a depth of 3 feet 10 inches. The shelves 200 A-C may also have a height of 11 feet 10 inches, a width of 7 feet 10 inches, and a depth of 5 feet 10 inches.

The aquaponics unit 1 may include plant floats 600 A-B. The plant floats 600 A-B are configured to have plants 700 grown within apertures on the plant floats 600 A-B. In this regard, the plant floats 600 A-B may have a plurality of apertures configured to have one or more plants 700 planted within each aperture. Because the plant floats 600 A-B float atop water within the shelves 200 A-C, the plant floats 600 A-B may be formed from a material that has enough buoyancy to float atop water when each aperture of the plant floats 600 A-B has one or more plants 700 which float atop the water within the shelves 200-A-C. The plant floats 600 A-B may have dimensions that allow the plant floats 600 A-B to be received by the shelves 200 A-C so that the plant floats 600 A-B are able to float freely atop the water within the shelf 200 A-C.

The aquaponics unit 1 may include a heating pump 400 for controlling the water temperature in the shelves 200 A-C and the fish tank 300. The heat pump 400 may have an outlet pipe 420 and may be connected to an inlet pipe 440. The outlet pipes 420 run from the heat pump 400 to and through the shelves 200 A-C, and through the fish tank 300. One of skill in the art will appreciate that the heat pump 400 may be any heat pump known in the art, including commercially available heat pumps. Both the outlet pipe 420 and the inlet pipe 440 may be formed from Cross-linked polyethylene (PEX). One of skill in the art will appreciate that the pipes may be made from polyvinyl chloride (PVC), chlorinated polyvinyl chloride (CPVC), copper tubing or any other pipes suitable for transporting water.

Figure 1:
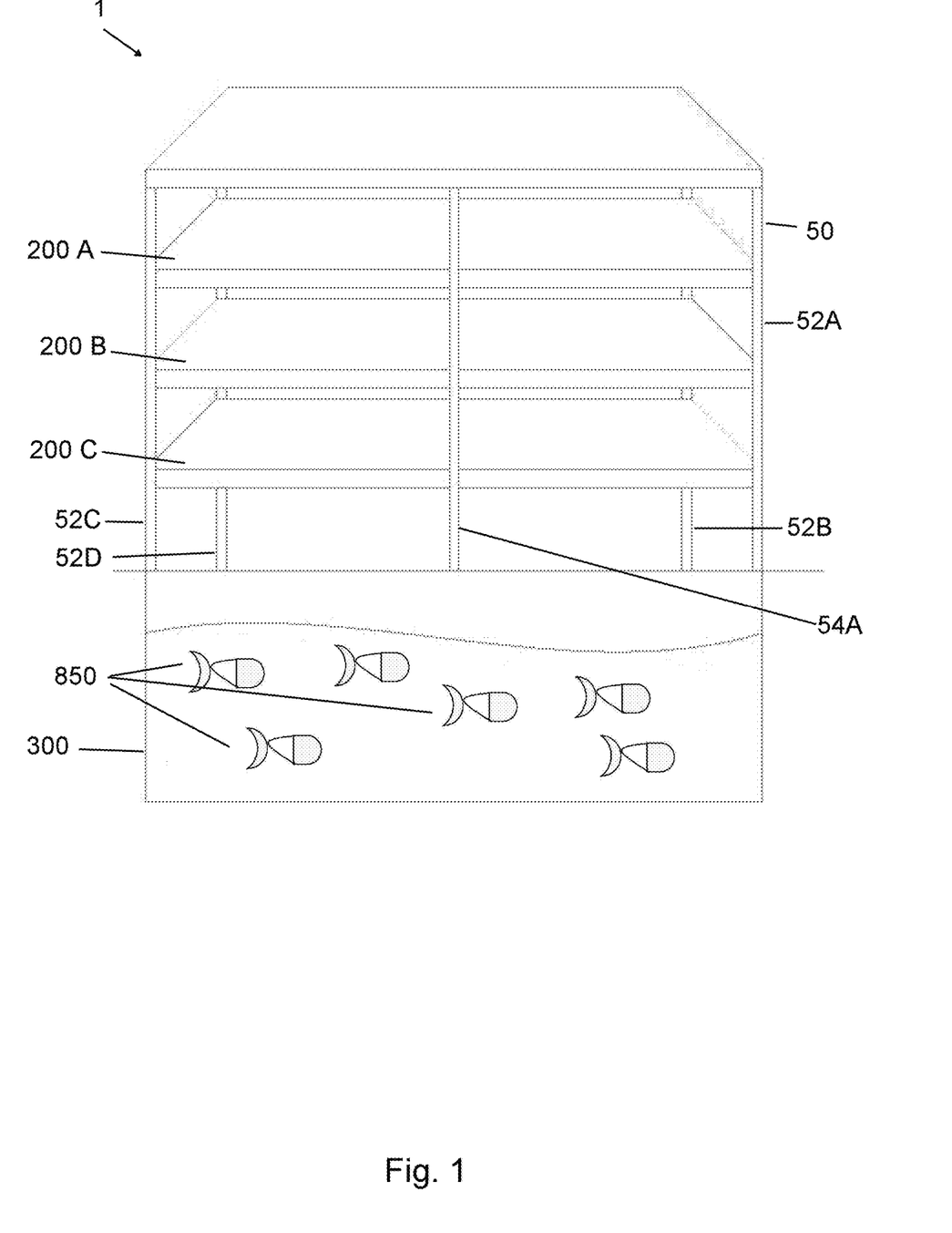
FIG. 1 illustrates the self-sustaining fish food system according to one embodiment.
Figure 2:
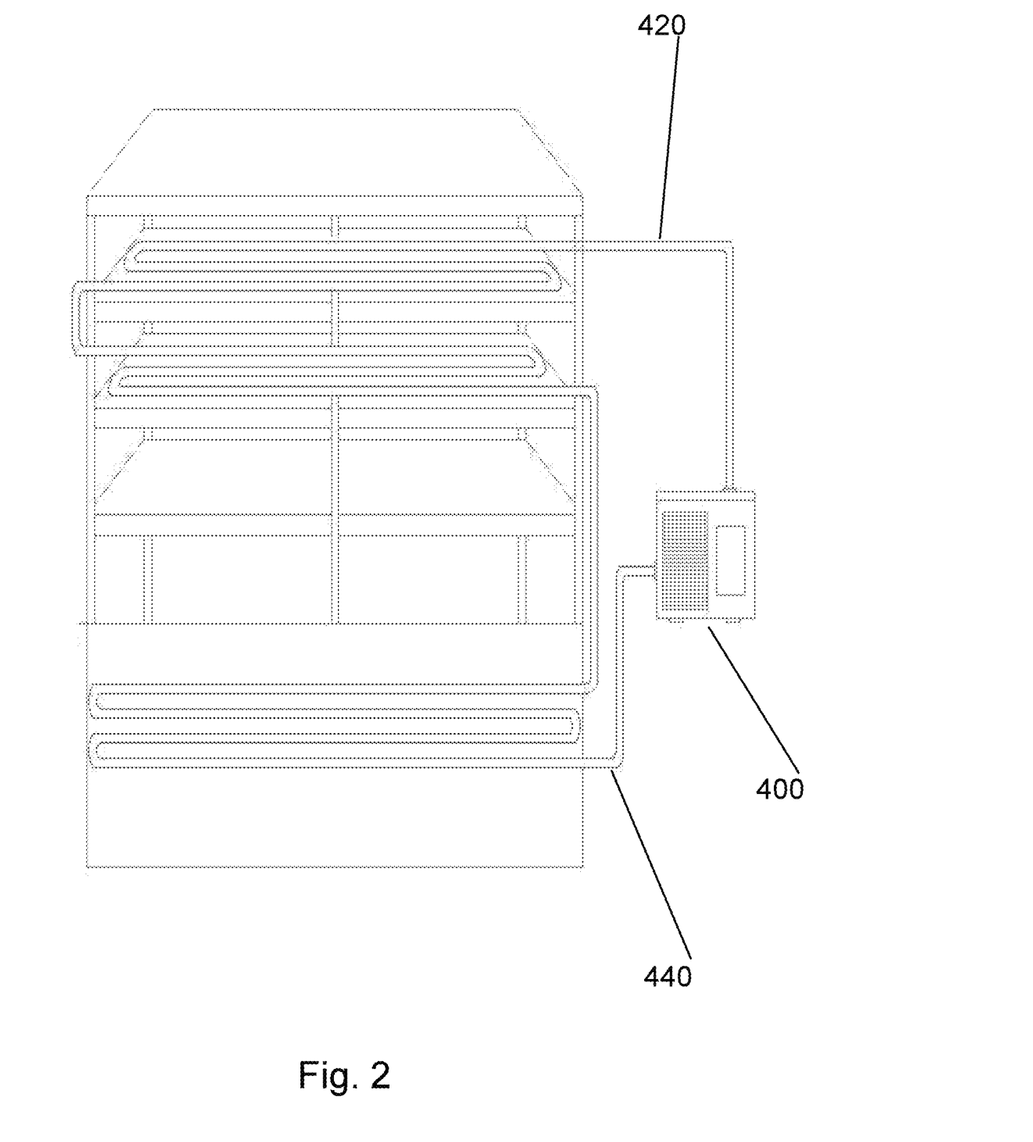
FIG. 2 illustrates the self-sustaining fish food system according to another embodiment.
Figure 3:
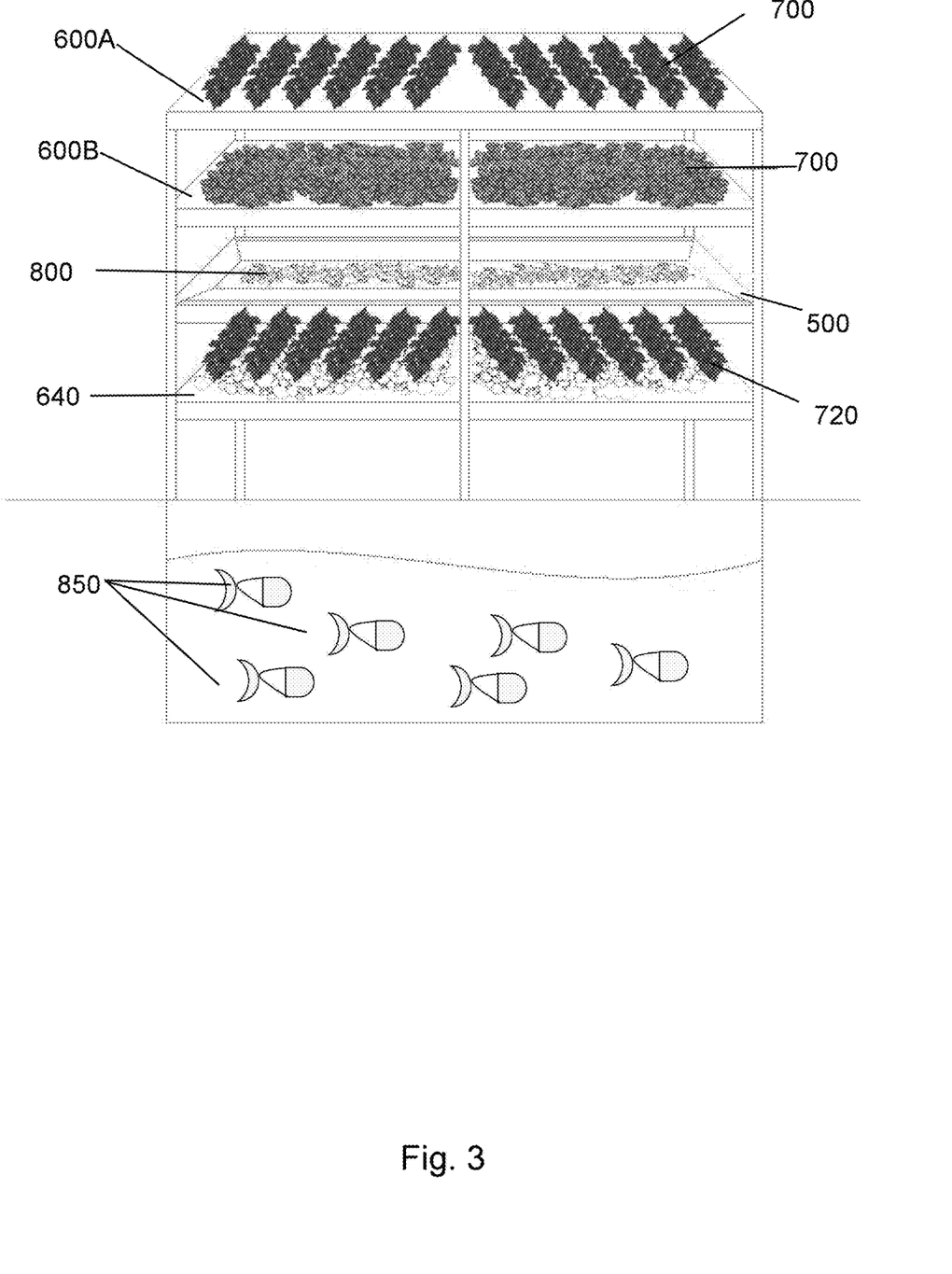
FIG. 3 illustrates the self-sustaining fish food system according to another embodiment.
Figure 4:
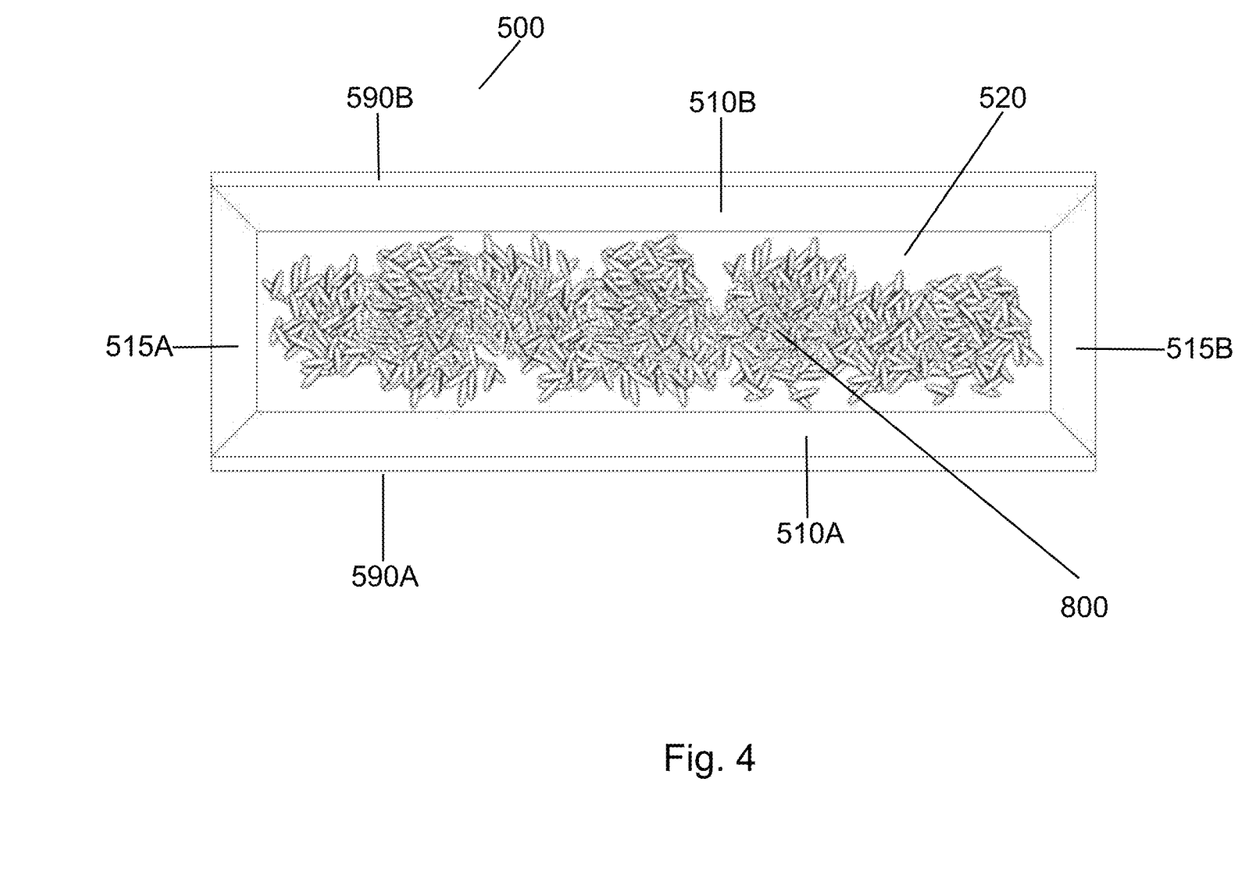
FIG. 4 illustrates the self-sustaining fish food system according to another embodiment.

The aquaponics unit 1 may include an insect tray 500. As shown in FIG. 4, the insect tray may be configured to hold insect eggs, larvae, or adult insects. In this regard, the insect tray 500 may be a rectangular shape that has walls configured to keep the living organisms inside the insect tray 500. The insect tray 500 may have a rectangular base 520. The rectangular base 520 may be attached to a set of primary slanted walls 510 A-B, and a set of secondary slanted walls 515A-B. In this regard, the insect tray 500 forms an open container for holding insect eggs, larvae, or adult insects. The insect tray 500 may have two primary slanted walls 510A-B that are opposite one another. The insect tray 500 may also have a secondary set of slanted walls 515A-B opposite one another. The slanted primary and secondary walls may be perpendicular to the base 520 of the insect tray 500. The slanted primary and secondary walls may form a forty-five degree angle with the base of the insect tray. The slanted primary and secondary walls may form a fifteen degree angle with the base 520 of the insect tray. Because the walls of the insect tray 500 are configured to allow adult insects and insect larvae 800 to crawl up the slanted walls, the walls may form an angle that is suitable to allow insects to crawl out of the insect tray 500. One of skill in the art will appreciate that the slanted walls of the insect tray may form an angle with the base 520 that is more or less than forty-five degrees.

The insect tray 500 may be configured to be accepted by one or more of the shelves 200 A-C. In this regard, the insect tray 500 may rest atop water within the tray 200. The insect tray 500 may have gutters 590A-B attached to the primary slanted walls 510A-B. The gutters may be configured for capturing anything that spills from the insect tray 500, including, but not limited to water, insect eggs, insect larvae, and adult insects. One or both gutters 590 A-B may have holes that allow insects to fall through to a fish tank below. The insect tray 500 may also be configured to be supported by the frame 50. When the insect tray is configured to be supported by the frame 50, the insect tray 500 is attached to the frame 50 at frame corner supports 52A-D and frame center supports 54A-B. When the insect tray 500 is configured to be accepted by a shelf 200 A-C, the insect tray 500 rests atop the water within the shelf with the outlet pipe 420 running beneath the insect tray in order to pump temperature controlled water beneath the insect tray 500. The insect tray 500 may be lined with a layer of waterproof material such as pond lining so that water may circulate beneath the waterproof material. The insect tray 500 may be in communication with temperature controlled water held in one or more of the shelves 200A-C.

The aquaponics unit 1 may include a fish tank 300. The fish tank 300 may be configured to hold water and fish in a manner that maintains water conditions for sustaining fish life. The fish tank 300 may be beneath the frame 50 of the aquaponics unit 1. The fish tank 300 may be partially below ground. Because the temperature of the fish tank 300 needs to be controlled, the fish tank 300 may be fully underground. The fish tank 300 may have dimensions that are suitable for holding enough fish to sustain the aquaponics unit 1. As a non-limiting example, the fish tank 300 may have a height of 3 feet, a width of 5 feet 10 inches, and a depth of 3 feet 10 inches. The shelves fish tank 300 may also have a height of 4 feet, a width of 7 feet 10 inches, and a depth of 5 feet 10 inches. The fish tank 300 may be fully below ground. The fish tank 300 may have a generally rectangular shape with four walls. The fish tank 300 may be configured to hold tilapia or other types of fish, including but not limited to blue gill, brim, sunfish, crappie, koi, and pacu.

The aquaponics unit 1 is configured to act as a closed loop system that uses fish to produce waste that feeds microbes or worms. These microbes and worms convert the waste to fertilizer for various types of plants 700. The fertilizer is circulated through the water of the aquaponics unit 1. The water, which contains fertilizer, contacts the plants 700 because the plants 700 float atop fertilizer containing water. In turn, the plants 700 act as a filtration system that return water to the fish held within a fish tank. An important aspect of the aquaponics unit 1 described herein is the way the fish are fed using insect larvae, insect eggs, and adult insects. The aquaponics unit 1 may be organized so the insect tray 500 is above the fish tank 300 to allow insect larvae, insect eggs, and adult insects to fall into the fish tank once the insect larvae, insect eggs, and adult insects fall over the primary slanted walls 510 A-B of the insect tray 500. Because insect larvae are sensitive to temperature changes, temperature change may be used to encourage the larvae 800 to crawl from the insect tray 500 and fall into the fish tank 600 below.

Figure 5:
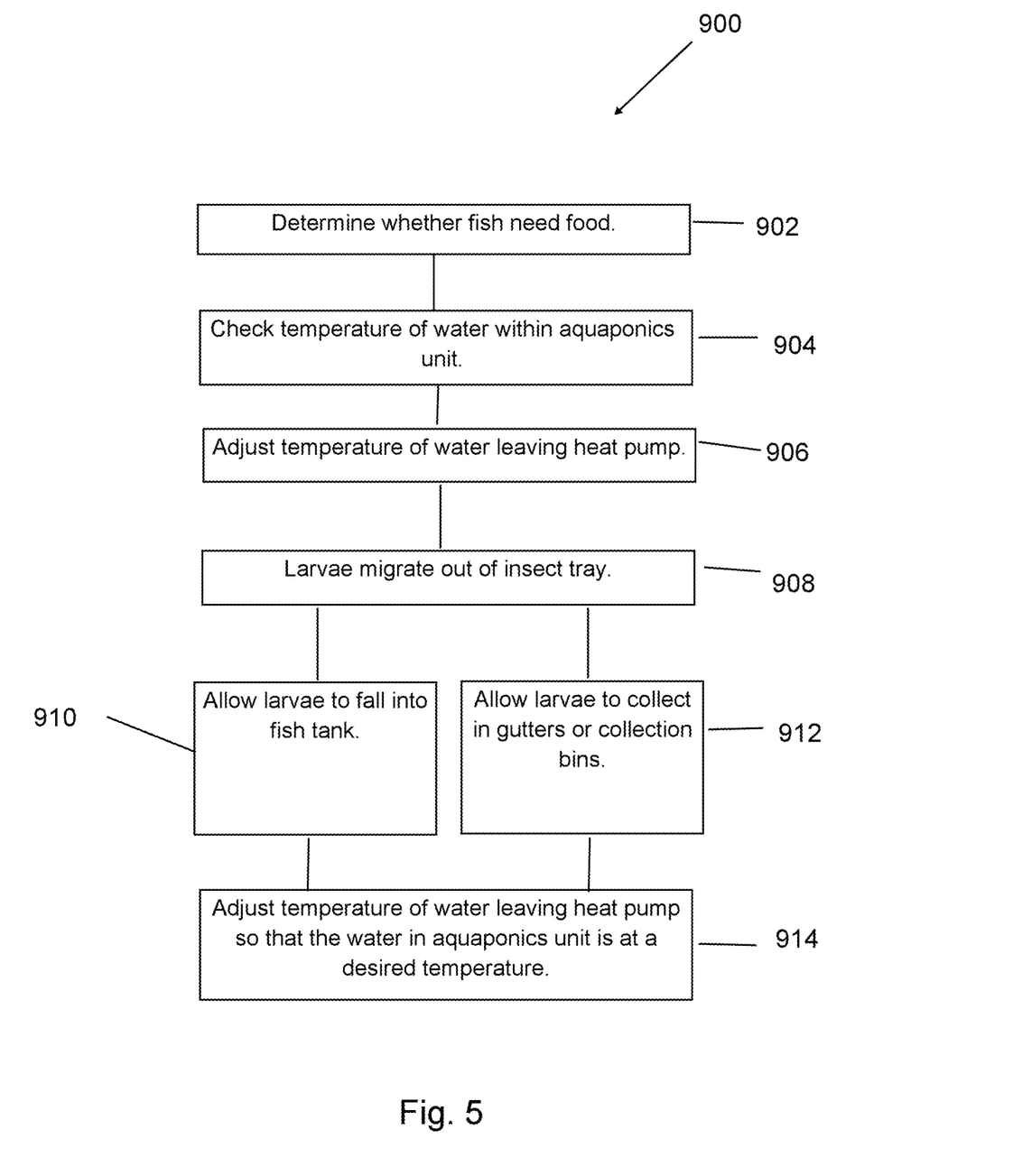
FIG. 5 illustrates a method associated with the self-sustaining fish food system according to another embodiment.

As shown in FIG. 5, in a first step 902, it is determined whether fish 850 need to be fed. A determination whether the fish 850 need food may be made according to a predetermined amount of time or according to the number of fish within the fish tank 300. In a next step 904, the water temperature within the aquaponics unit may be checked using a thermometer or other temperature measuring devices known in the art.

In a next step 906, the temperature of the water leaving the heat pump may be adjusted. The adjustment of the temperature of water leaving the heat pump may increase or decrease the water temperature within the aquaponics unit 1. In a next step 908, the alteration of the water temperature may cause larvae 800 within the insect tray 500 to migrate out of the tray.

In a next step 910, the larvae may be allowed to fall into the fish tank below 300. In another step 912, the larvae 800 may be collected for later use. In a next step 914, the temperature of the water leaving the heat pump 400 may be adjusted so that the water in the aquaponics unit 1 is at a desired temperature.

As a non-limiting example, the temperature of the water beneath the insect tray 500 may be controlled by adjusting the temperature of the heat pump 400 so that water pumped from the heat pump 400 flows to the outlet pipe 420, which may be beneath the insect tray 500. The increased or decreased temperature of the water flowing through the outlet pipe 420 may change the temperature of the water within the walls of the insect tray because the outlet pipes 420 run through the water held within the insect tray 500 or the water held within the shelf 200 holding the insect tray 400. As a non-limiting example, the water within the outlet pipe 420 may be kept at eighty degrees Fahrenheit. The temperature of the water of within the outlet pipe 420 may be kept around eighty degrees Fahrenheit to prevent natural over/under heating due to feeding and outside climate elements in the greenhouse. One of skill in the art will appreciate that the temperature of the water flowing through the outlet pipe 420 may be kept at a temperature that maintains an appropriate temperature of the water outside the outlet pipe 420 and inside the insect tray 500 or shelf 200. The temperature of the water flowing through the outlet pipe 420 may be temporarily raised to encourage insect larva to migrate out of the insect tray 500 into the fish tank below. A temporary temperature change may also encourage larva to migrate from the insect tray 500 to the gutters 590A-B, where the larva are held until they are used for feeding the fish.

As a non limiting example, black soldier fly larva 800 may be included with the aquaponics unit 1. *Hermetia illucens*, the black soldier fly, is a common and widespread fly of the family Stratiomyidae. Neither the larvae nor adults are considered pests or vectors. Instead, black soldier fly larvae play a similar role to that of redworms as essential decomposers in breaking down organic substrates and returning nutrients to the soil/environment. Black soldier fly larvae (BSFL), are a source of sustainable protein for aqua culture/animal feed, pet and human nutrition. As the larvae have voracious appetites they can also be used for composting household food scraps and agricultural waste products. Black soldier fly eggs take approximately four days to hatch and are typically deposited in crevices or on surfaces above or adjacent to decaying matter such as manure or compost. The larvae range in size from ⅛-¾ inch (3-19 mm). Although they can be stored at room temperature for several weeks, their longest shelf life is achieved at fifty-sixty degrees Fahrenheit (ten-sixteen degrees Celsius).

Black soldier fly larvae (BSFL) 800 may be used to compost and sanitize wastes, and/or convert the wastes into animal feed. The harvested pupae and prepupae are eaten by poultry, fish, pigs, turtles; even dogs. When the larvae have completed their larval development through six instars, they enter a stage called the "prepupae" wherein they cease to eat, they empty their guts, their mouth parts change to an appendage that aids climbing, and they seek a dry, sheltered area to pupate. This prepupae migration instinct is used by grub composting bins to self-harvest the mature larvae.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A self-harvesting sustaining feed system for an aquaponics system comprising:
   a tank;
   a frame above the tank;
   one or more plant floats in communication with the frame;
   an insect tray lined with at least one layer of waterproof material, the insect tray held by the frame and resting atop water, the insect tray having two opposing primary slanted walls, two opposing slanted secondary walls, a base, a first gutter attached to a first of the two opposing primary slanted walls and a second gutter attached to a second of the two opposing primary slanted walls, the two opposing primary slanted walls of the insect tray and the two opposing slanted secondary walls extending from the base, the two opposing primary slanted walls and the two opposing secondary slanted walls forming a forty-five degree angle with the base, and configured to allow insects to crawl up the slanted walls and fall into the tank via the first gutter and the second gutter; and
   one or more shelves held by the frame, the insect tray configured to be accepted by the one or more shelves and attached to the frame using at least one frame corner support and at least one frame center support.

2. The self-harvesting sustaining feed system of claim 1, wherein the slanted walls have one or more apertures.

3. The self-harvesting sustaining feed system of claim 1, wherein the system further comprises a water heating system to heat water in the tank.

4. The self-harvesting sustaining feed system of claim 3, wherein the water heating system has an inlet pipe and an outlet pipe.

5. The self-harvesting sustaining feed system of claim 1, wherein the tank houses fish.

6. The self-harvesting sustaining feed system of claim 1, wherein the insect tray houses insect larvae.

7. The self-harvesting sustaining feed system of claim 1, wherein the one or more shelves have side walls.

8. The self-harvesting sustaining feed system of claim 4, wherein the one or more shelves have apertures for accepting an outlet pipe from the water heating system.

9. The self-harvesting sustaining feed system of claim 1, wherein the frame is above the tank.

10. The self-harvesting sustaining feed system of claim 1, wherein the tank houses fish comprising at least one of tilapia, blue gill, brim, sunfish, crappie, koi, and pacu.

11. The self-harvesting sustaining feed system of claim 1, wherein the one or more shelves are formed from a waterproof material.

12. The self-harvesting sustaining feed system of claim 1, wherein the one or more shelves are lined with a waterproof material.

13. The self-harvesting sustaining feed system of claim 1, wherein the insect larvae are black soldier fly larvae.

14. The self-harvesting sustaining feed system of claim 1, wherein the one or more plant floats rest atop at least one of the one or more shelves and house one or more plants.

* * * * *